United States Patent
Trouilloud et al.

(10) Patent No.: US 9,381,026 B2
(45) Date of Patent: Jul. 5, 2016

(54) JIG FOR PLACING A SHOULDER PROSTHESIS ONTO A SOCKET

(75) Inventors: Pierre Trouilloud, Dijon (FR); Martin Gonzalvez, Dijon (FR); Christophe Alepee, Lyons (FR)

(73) Assignee: Aston Medical, Saint-Etienne (FR)

( * ) Notice: Subject to any disclaimer, the term of this patent is extended or adjusted under 35 U.S.C. 154(b) by 299 days.

(21) Appl. No.: 13/883,125

(22) PCT Filed: Oct. 21, 2011

(86) PCT No.: PCT/FR2011/052461
§ 371 (c)(1),
(2), (4) Date: Jun. 26, 2013

(87) PCT Pub. No.: WO2012/059661
PCT Pub. Date: May 10, 2012

(65) Prior Publication Data
US 2013/0274752 A1   Oct. 17, 2013

(30) Foreign Application Priority Data
Nov. 5, 2010   (FR) ...................................... 10 59147

(51) Int. Cl.
*A61B 17/17* (2006.01)

(52) U.S. Cl.
CPC ..... *A61B 17/1739* (2013.01); *A61B 2017/1778* (2013.01)

(58) Field of Classification Search
CPC .................... A61B 2017/1778; A61B 17/1739
See application file for complete search history.

(56) References Cited

U.S. PATENT DOCUMENTS

| 6,059,789 A * | 5/2000 | Dinger et al. ................... 606/96 |
| 2004/0193175 A1 | 9/2004 | Maroney et al. |
| 2005/0137606 A1 * | 6/2005 | Binder et al. ................... 606/96 |
| 2005/0245936 A1 * | 11/2005 | Tuke et al. ...................... 606/89 |
| 2007/0233136 A1 * | 10/2007 | Wozencroft .................... 606/86 |
| 2009/0118736 A1 * | 5/2009 | Kreuzer ........................... 606/96 |

FOREIGN PATENT DOCUMENTS

| EP | 1813215 A1 | 8/2007 |
| FR | 2898267 A1 | 9/2007 |
| WO | WO-2005051209 A1 | 6/2005 |

OTHER PUBLICATIONS

International Search Report and Written Report of the International Searching Authority for PCT/FR11/052461 dated Dec. 21, 2011 (15 pages).

* cited by examiner

*Primary Examiner* — Christian Sevilla
(74) *Attorney, Agent, or Firm* — Harris Beach PLLC

(57) ABSTRACT

The jig includes bearing portions capable of engaging, only on the anatomical bone structure of the patient, with the front and rear edges of the socket, said portions having temporary positioning and attaching arrangements defining contact surfaces engaging with said front and rear edges, and said portions being formed from an area for connecting with a gripping sleeve arranged to act as a bore guide, wherein the positioning and orientation of the sleeve are predetermined relative to a three-dimensional coordinate system specific to the scapula and resulting from a peroperative plan translated via a bore axis defined by a vector and an origin that is the center of the socket, wherein both the vector and the origin give said orientation to the customized placement jig.

10 Claims, 2 Drawing Sheets

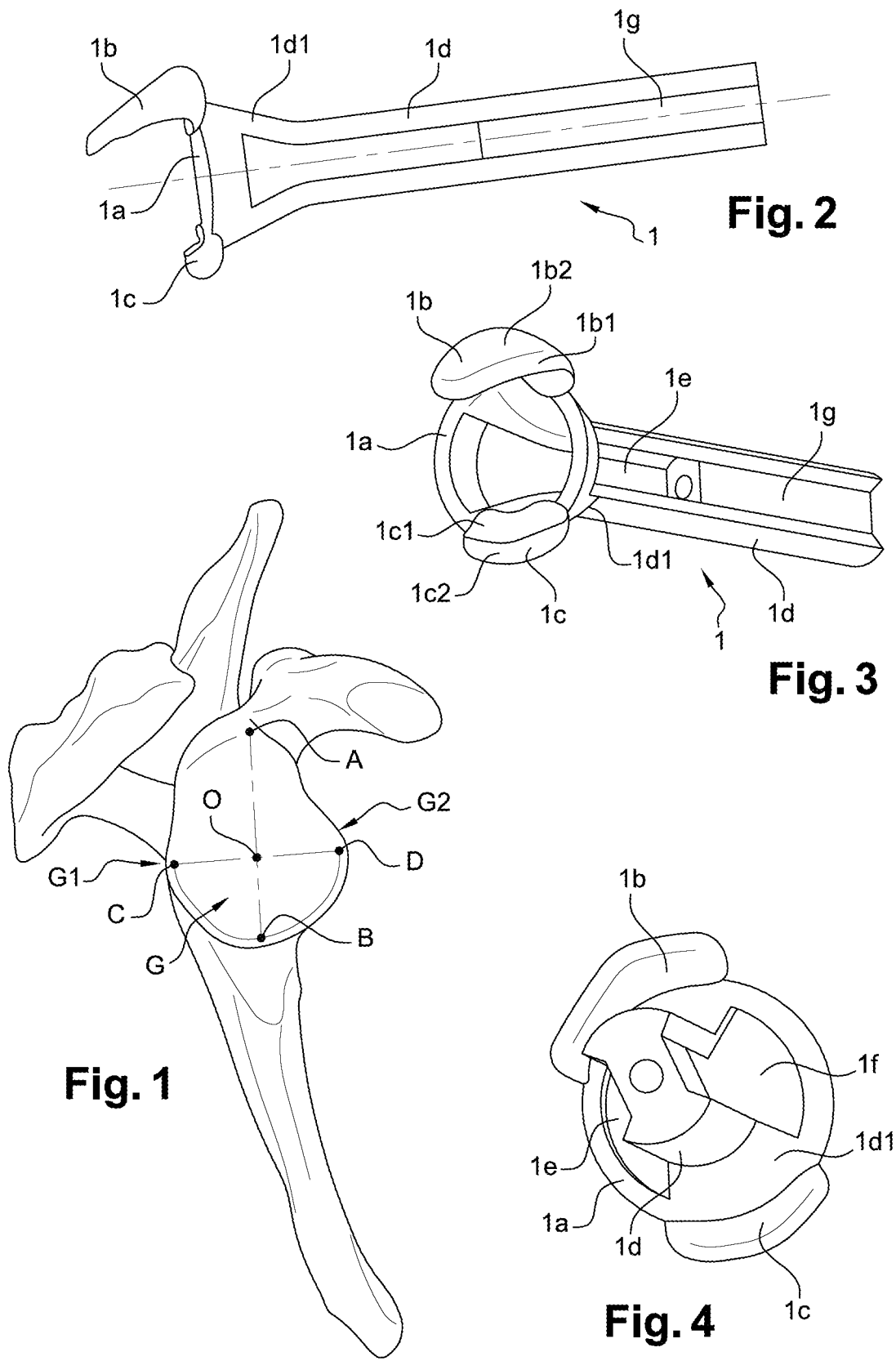

JIG FOR PLACING A SHOULDER PROSTHESIS ONTO A SOCKET

CROSS-REFERENCE TO RELATED APPLICATIONS

This application is a national stage application under 35 U.S.C. §371 of PCT Application No. PCT/FR2011/052461, filed Oct. 21, 2011, which claims priority to and the benefit of French Application No. 1059147 filed on Nov. 5, 2010, which are incorporated herein by reference in its entirety.

The invention relates to the technical field of instruments for the placing of orthopedic implants.

More specifically, the invention relates to a customized guide or jig for placing a shoulder prosthesis, especially of inverted type, where the condyle as such is attached at the level of the glenoid cavity to cooperate with a cup of complementary shape of the humeral element of the prosthesis. Other types of prostheses may be envisaged, such as anatomic prostheses, resurfacing prostheses.

This type of prosthesis for example appears from the teachings of patent FR 2618065. The condyle may be attached in the glenoid cavity either directly, or via a support base. Now, the attaching and the positioning of this support base receiving the condyle or directly of the cup appear to be particularly important for the success of the biomechanical operation of the shoulder prosthesis and the lifetime of the implant, whatever its type. Generally, the support or other is attached in the glenoid cavity by means of standard surgical instruments.

An important step of the installation procedure is the orientation of the boring of a hole in the glenoid cavity to determine the milling angle which conditions the positioning of the prosthesis.

Generally, a surgeon uses a bore guide, but the design thereof does not enable to precisely reproduce a preliminary plan. Indeed, according to the state of the art, prior to the installing of the prosthesis, the surgeon plans the surgery from a bidimensional image of the joint, for example, by means of a radiography, of a scanner, or of a MRI. Studies have demonstrated the high importance of positioning the glenoid support of the prosthesis on the glenoid cavity with respect to precise anatomical points of reference, from which measurements can be made. Now, the results obtained in the case of a plan based on a bidimensional imaging remain inaccurate and do not enable to achieve the objects of the plan. For example, the orientation of the 2D cross-sections has a direct incidence on the measurement made.

The invention aims at overcoming these disadvantages in a simple, sure, efficient, and rational manner by planning in three dimensions the placing of the prosthesis based on images originating from scanners or MRIs. To achieve this, the 2D images are processed by means of specific software enabling to segment the bone areas of interest for the installation, with the purpose of reconstructing a three-dimensional structure. On this structure are defined reference points enabling to define a coordinate system specific to the scapular bone. This three-dimensional model enables to accurately simulate, plan, and measure the orientation of the prosthesis according to the previously-mentioned coordinate system. This plan translates as the mathematical definition of a bore axis defined by a vector and an origin. Around this axis is designed a customized placement guide or jig for physically restoring this axis, peroperatively, to enable to optimally install the implant.

To achieve these objects, the placement guide according to the invention comprises bearing portions capable of engaging only with the glenoid cavity and areas of its circumference, said portions having temporary positioning and attachment arrangements defining contact surfaces engaging with the rear and front edges of the glenoid cavity, said portions being formed from an area of connection to a gripping handle arranged to act as a bore guide, the positioning and orientation of the handle are determined relative to a three-dimensional coordinate system resulting from a peroperative plan and connected to the scapular bone from anatomical reference point having as an origin the center of the glenoid cavity.

As a result of these characteristics, the temporary positioning and attachment arrangements are not oriented with respect to the coordinate system, but only defined by the shapes of the contact areas on the rear and front rims of the glenoid cavity. The handle (guide) is oriented according to the plan in the coordinate system of the scapular bone as defined.

The guide thus constructed only adapts on the patient's anatomic bone structure.

The placement jig according to the invention thus enables to materialize the unreal positioning of the planned bore axis relative to the patient's anatomical areas.

To solve the posed problem of positioning the jig relative to the reference points determined within the framework of the preparatory three-dimensional plan, the temporary positioning and attachment arrangements are opposite and shaped to provide a snapping effect on the rims of the glenoid cavity.

The arrangements are formed by hook-shaped oriented tabs formed from the connection area. The front tab of sufficient length cooperates with the front rim of the glenoid cavity and with a portion of the front surface of the scapular bone, and has an area for bearing on the front rim of the glenoid cavity. Similarly, the shorter rear tab is sufficient to cooperate with the rear rim of the glenoid cavity, and has an area defined with the rear rim of the glenoid cavity.

In an embodiment of the placement jig, to solve the posed problem of boring the glenoid support from the placement jig, the connection area forms a ring of substantially circular general shape. The gripping handle is connected to the connection area by a tapered extension. The tapered extension and the base of the handle have two opposite openings located on either side of the contact areas formed by the tabs.

Such openings may especially enable to visually control the positioning of the jig, and to visually control the boring point. They also provide a resilience between the rear and front rims, thus easing the installation of the jig on the bone structure.

It can also be observed that the handle, which integrates the previously-planned bore axis, provides a stable positioning of the boring tool to perform said boring according to the previously established plan.

It can be seen from the features of the invention that the placement guide or jig precisely adapts on the patient's anatomical structure, accordingly forming a customized placement jig in that, for each patient, a new jig is formed.

The invention is discussed hereafter in further detail by means of the appended drawings, among which:

FIG. 1 shows a scapular bone with, especially, the anatomical reference points at the level of the glenoid cavity.

FIG. 2 is a front view of the placement jig according to the invention.

FIG. 3 is a bottom perspective view of the considered jig, that is, seen from the bearing areas.

FIG. 4 is a top perspective view of the considered jig, that is, seen from the bore guide.

Figure 5:
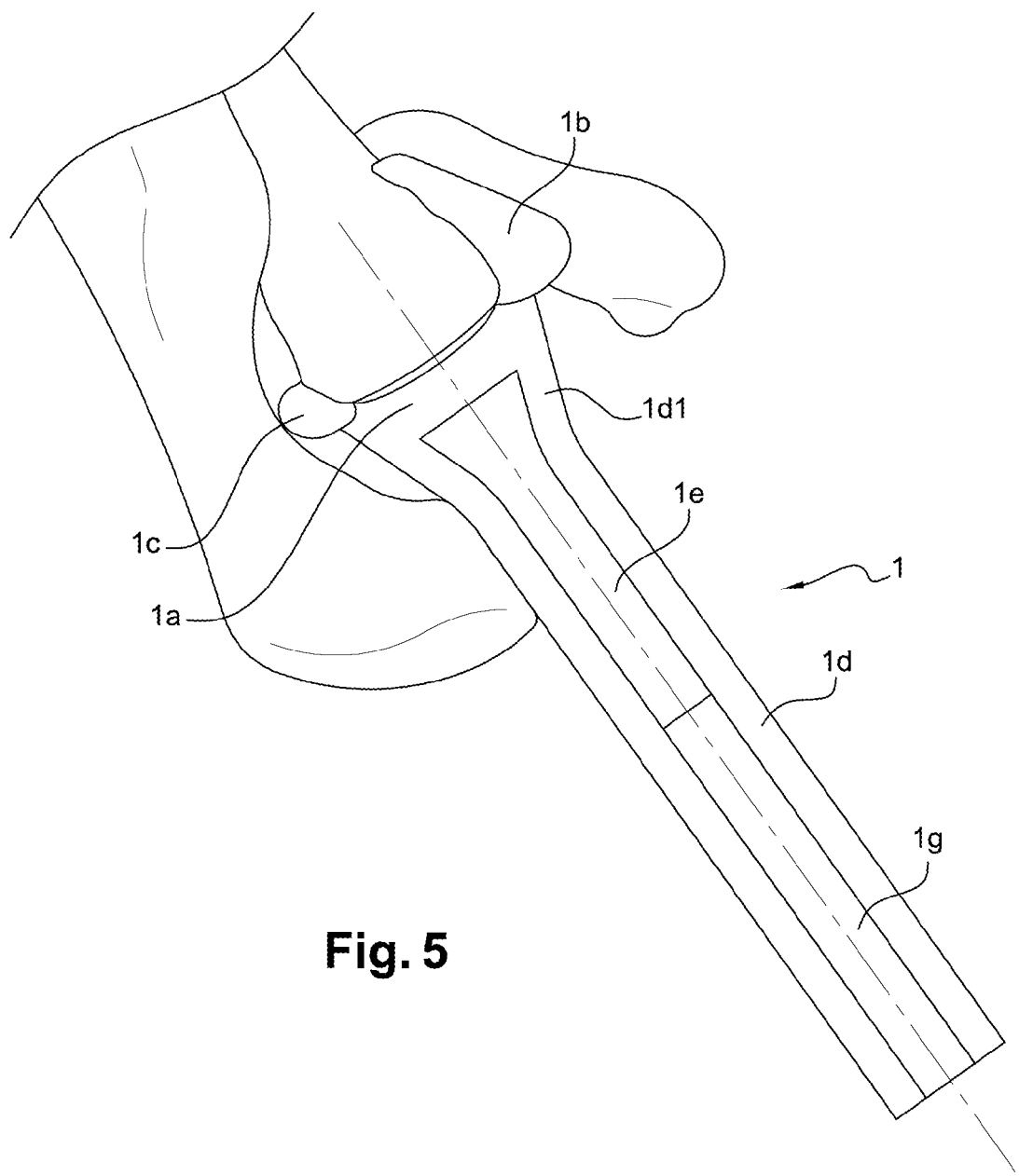
FIG. 5 shows the placing of the placement jig with respect to the glenoid cavity.

As indicated, the placement jig according to the invention is formed based on a peroperative plan designed on a three-dimensional reconstruction made from images originating from a scanner, from MRI, . . . , which plan is summed up by the unique definition of a bore axis, defined by a vector and an origin which give the orientation of the customized placement jig and based on which the customized placement jig will be positioned.

It is thus particularly important to define the center (O) of the glenoid cavity (G), which is defined from 4 points respectively formed by the upper rim of the glenoid cavity (A), at the foot of the coracoid, the lower rim of the glenoid cavity (B), the rear rim (C) in front of the acromion spine of the glenoid cavity, and the front rim (D) of the glenoid cavity. Thus, the crossing of the two straight lines (A-B) and (C-D) defines the center of the glenoid cavity. The reference coordinate system is determined by its origin (O) and two other anatomical reference points of the scapular bone, that is, the Trigonum Scapulae and the lower angle. It is accordingly possible to define both a relative orientation of the glenoid cavity with respect to the scapular bone and the inclination of the glenoid cavity with respect to the previously-mentioned coordinate system. Based on this reference system, the prosthesis can thus be positioned in three dimensions. It is accordingly possible to position the bore axis from which the placement jig according to the invention will be indexed and to define an orientation with a vector in the previously-defined reference system.

Reference should be made to the drawings, which show the features of the jig for placing a shoulder prosthesis, inverted or not, to ensure, as previously indicated, the boring of the glenoid cavity.

This jig, generally designated with reference (1) comprises bearing portions capable of engaging with the rims of the glenoid cavity (G). The bearing portions have, in opposite fashion, temporary positioning and attachment arrangements engaging with the rear (G1) and front (G2) rims of the glenoid cavity (G). Such arrangements (1b) and (1c) are determined to provide a temporary attachment of the entire jig by snapping effect and have bearing areas delimiting two subassemblies (1b1-1b2) and (1c1-1c2) separating the edge and the rim of the glenoid cavity.

Such arrangements (1b) and (1c) are formed by oriented hook-shaped tabs formed from an area of connection (1a) with a handle (1d). The tab (1b), engaging with the front edge of the glenoid cavity, has a bearing area (1b1) extending on the rim. The front tab (1b) has a substantially triangular facial profile. The opposite tab (1c), which engages with the rear edge, is of smaller length by forming a bead with a profiled cross-section to ensure the snapping effect.

Bearing portions (1b) and (1c) uniquely cooperate with the rims of the glenoid cavity and are continued by the gripping handle (1d) arranged to behave as a bore guide.

The positioning and the orientation of the handle (1d) are determined according to the three-dimensional coordinate system resulting from the peroperative plan, as indicated previously. The gripping handle (1d) is connected to area (1a) by a tapered extension (1d1). The tapered extension (1d1) and the lower portion of the handle (1d) have two opposite openings (1e) and (1f) located on either side of the contact areas formed by tabs (1b) and (1c). Such openings (1e) and (1f) enable to observe the proper positioning of the jig and contribute to improving the resilience to obtain the desired snapping effect.

As indicated, the upper portion of the gripping handle is arranged to behave as a bore guide. For example, this bore guide is formed by a solid area (1g) coaxially bored concentrically to area (1a). It should be noted that area (1a) is formed by a ring having a generally circular shape corresponding to the lower portion of the glenoid cavity.

It can be observed that the front and rear bearing areas are constructed by selecting and extruding by approximately three millimeters the selected surface of the 3D structure. The increased volume of the scapular bone is subtracted from these 3D volumes. Increased volume designates an interval between the 3D digital model and the real model, which results from the accuracy of the scanner or other and from possible biological tissues not detected by the scanner. The performed trials have shows that this interval ranges between approximately 0.3 and 1 millimeter.

As a non-limiting indication, the following dimensional features have provided satisfactory results:

Jig length from bearing portion (1a) to the end of the handle, approximately 10 cm, allowing a positioning from the outside of the incision.

Length of the bore jig (1g), approximately 5 cm

Handle diameter, approximately 15 millimeters.

Conical extension (1d1) forming an angle of approximately 20° with respect to the handle axis (1d).

Thickness of the bearing and attachment tabs (1b) (1c) approximately ranging from 3 to 4 millimeters.

Triangular shape of the tab (1b) forming a base having a length ranging between approximately 20 and 25 millimeters and a height ranging between approximately 20 and 25 millimeters.

Bearing tab having a length approximately ranging from 10 to 15 millimeters and a width approximately ranging from 5 to 10 millimeters.

Reference should be made to FIG. 5 which shows the adapting of a placement jig according to the features of the invention, with respect to the glenoid cavity (G).

The advantages are well highlighted by the description, and it should especially be underlined and reminded that a customized placement jig which reproduces during the surgery the peroperative plan made from a three-dimensional coordinate system linked to the scapular bone is obtained. The coordinate system will be precisely found by the surgeon by the coaptation of the anatomical bone shape with the bearing area of the jig of complementary shape.

The invention claimed is:

1. A custom positioning jig for a shoulder prosthesis on a glenoid, comprising:

a plurality of bearing parts cooperating with the glenoid, said plurality of bearing parts cooperate, in a unique and custom manner, on a patient's anatomical bone structure with an anterior lip and a posterior lip of the glenoid, by means of a first oriented arm and a second oriented arm, forming a pair of oriented hook-shaped tabs, the first oriented arm cooperates with an anterior edge of the glenoid, the second oriented arm cooperates with a posterior edge of the glenoid, each of said first oriented arm and said second oriented arm have bearing areas which delineate a first oriented bearing arm sub assembly and a second bearing arm sub assembly respectively which separate an edge and lip of the glenoid; and a gripping handle coupled to said plurality of bearing parts to form a custom positioning jig to act as a drilling guide, a positioning and an orientation of the gripping handle determined with respect to a three-dimensional coordinate system specific to a scapula of the patient to be operated on resulting from intraoperative planning giving a drilling center line defined by a vector and an origin, determining a center of the glenoid and the orientation in space of the custom positioning jig.

2. The custom positioning jig for placing a shoulder prosthesis of claim 1, characterized in that temporary positioning and attachment arrangements are opposite and profiled to provide a snapping effect.

3. The custom positioning jig for placing a shoulder prosthesis of claim 1, characterized in that an area of connection with the gripping handle forms a ring of substantially circular shape.

4. The custom positioning jig for placing a shoulder prosthesis of claim 1, characterized in that the gripping handle is connected to an area of connection by a tapered extension.

5. The custom positioning jig for placing a shoulder prosthesis of claim 4, characterized in that the tapered extension and a base of the gripping handle have two opposite openings located on either side of a plurality of contact areas formed by said pair of oriented hook-shaped tabs, providing a resilience easing an installation of said jig.

6. The custom positioning jig for placing a shoulder prosthesis of claim 1, characterized in that an arrangement is formed by said pair of oriented hook-shaped tabs formed from a contact surface of a contact area.

7. The custom positioning jig for placing a shoulder prosthesis of claim 3, characterized in that a tab of said pair of oriented hook-shaped tabs cooperating with a front edge of a glenoid cavity and with a portion of a front surface of a scapular bone, extends by bearing on a rim of the glenoid cavity.

8. The custom positioning jig for placing a shoulder prosthesis of claim 3, characterized in that a tab of said pair of oriented hook-shaped tabs cooperating with a rear edge of a glenoid cavity is of a shorter length, capable of cooperating with a rear rim of the glenoid cavity.

9. The custom positioning jig for placing a shoulder prosthesis of claim 1, characterized in that said drilling guide is incorporated to an upper portion of the gripping handle.

10. The custom positioning jig for placing a shoulder prosthesis of claim 1, characterized in that a length of the gripping handle is determined to allow a positioning from the outside of an incision.

* * * * *